US009862987B2

(12) United States Patent
Lo et al.

(10) Patent No.: US 9,862,987 B2
(45) Date of Patent: *Jan. 9, 2018

(54) LABEL FREE MOLECULAR DETECTION METHODS, SYSTEMS AND DEVICES

(71) Applicant: The Regents of the University of California, Oakland, CA (US)

(72) Inventors: Yu-Hwa Lo, San Diego, CA (US); Wen Qiao, La Jolla, CA (US); Junlan Song, La Jolla, CA (US); Longchuan Chen, Long Beach, CA (US)

(73) Assignees: The Regents of the University of California, Oakland, CA (US); Departments of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/761,603

(22) PCT Filed: Jan. 16, 2014

(86) PCT No.: PCT/US2014/011942
§ 371 (c)(1),
(2) Date: Jul. 16, 2015

(87) PCT Pub. No.: WO2014/113614
PCT Pub. Date: Jul. 24, 2014

(65) Prior Publication Data
US 2015/0361483 A1 Dec. 17, 2015

Related U.S. Application Data

(60) Provisional application No. 61/753,384, filed on Jan. 16, 2013.

(51) Int. Cl.
C12Q 1/68 (2006.01)

(52) U.S. Cl.
CPC ......... *C12Q 1/6806* (2013.01); *C12Q 1/6825* (2013.01)

(58) Field of Classification Search
CPC .. C12Q 1/68; C12M 1/00; C12M 1/34; G01Q 60/08; G01N 27/83; G01N 33/54333
See application file for complete search history.

(56) References Cited

U.S. PATENT DOCUMENTS 6,007,690 A * 12/1999 Nelson ............. G01N 27/44791
204/450
2004/0241699 A1 12/2004 Zocchi et al.
(Continued)

FOREIGN PATENT DOCUMENTS

EP 2390350 * 11/2011
WO 199106679 A1 5/1991
(Continued)

OTHER PUBLICATIONS

Ding et al., "Single-molecule mechanical identification and sequencing," Nature Methods, vol. 9, No. 4, 367-374. Apr. 2012.
(Continued)

*Primary Examiner* — Narayan Bhat
(74) *Attorney, Agent, or Firm* — Perkins Coie LLP

(57) ABSTRACT

Methods, systems, and devices are disclosed for capturing, concentrating, isolating, and detecting molecules. In one aspect, a molecular probe device includes a molecular probe having a complimentary base pair region initially zipped and structured to include a binding agent to chemically attach the molecular probe to an outer surface of a magnetic bead, and a binding molecule to chemically attach the molecular probe to a substrate of a microfluidic device, in which the complimentary base pair region is configured to hybridize to a complementary nucleic acid sequence of a DNA or RNA molecule.

22 Claims, 8 Drawing Sheets

(56) References Cited

U.S. PATENT DOCUMENTS

| | | |
|---|---|---|
| 2008/0202933 A1 | 8/2008 | Hu |
| 2009/0071830 A1 | 3/2009 | Vann et al. |
| 2009/0152215 A1 | 6/2009 | Ahn et al. |
| 2009/0269767 A1 | 10/2009 | Soderlund et al. |
| 2010/0173310 A1 | 7/2010 | Bousse et al. |
| 2010/0181195 A1 | 7/2010 | Garcia-Tello |
| 2011/0039717 A1 | 2/2011 | Kwong et al. |
| 2012/0208189 A1 | 8/2012 | Xu et al. |
| 2012/0258459 A1 | 10/2012 | Huang |

FOREIGN PATENT DOCUMENTS

| | | |
|---|---|---|
| WO | 200598029 A2 | 10/2005 |
| WO | 2011147931 A1 | 12/2011 |

OTHER PUBLICATIONS

Linnarsson, Stan, "Magnetic sequencing," Nature Methods, vol. 9, No. 4, 339-341, Apr. 2012.

Cantin et al., "Discrimination between exosomes and HIV-1: Purification of both vesicles from cell-free supernatants." Journal of Immunological Methods, vols. 1-2, 2008, pp. 21-30.

Chen et al. 10, "Microfluidic isolation and transcriptome analysis of serum microvesicles." s.l. : The Royal Society of Chemistry, 2010, Lab on a Chip, pp. 505-511.

Cho et al., "Human Mammalian Cell Sorting using Microfabricated Fluorescence Activated Cell Sorter." 2010, Lab on a Chip, vol. DOI:10, p. 1039:C000136H.

Geekiyanage et al., "Blood serum miRNA non-invasive biomarkers for Alzheimer's disease.", Experimental Neurology, 235(2), Jun. 2012, pp. 491-496.

Heinze et al., "Nanoparticle immunoagglutination Rayleigh scatter assay to complement microparticle immunoagglutination Mie scatter assay in a microfluidic device." 2011, Colloids and Surfaces B: Biointerfaces, pp. 168-173.

Kosaka et al., "Circulating microRNA in body fluid: a new potential biomarker for cancer diagnosis and prognosis." Oct. 2010, Cancer Sci., vol. 101, pp. 2087-2092.

Krishnan et al., "Alternating current electrokinetic separation and detection of DNA nanoparticles in high-conductance solutions." 2008, Electrophoresis, pp. 1765-1774.

Krishnan et al., "Rapid Isolation and Detection of Cell Free Circulating DNA and Other Disease Biomarkers Directly from Whole Blood." 2011, Circulating Nucleic Acids in Plasma and Serum, pp. 247-257. DOI: 10.1007/978-90-481-9382-0_34.

Kuo et al., "A microfabricated CE chip for DNA pre-concentration and separation utilizing a normally closed valve." 2009, Electrophoresis, pp. 3228-3235.

Ma et al., "Circulating microRNAs in cancer: origin, function and application." 2012, Journal of Experimental & Clinical Cancer Research, vol. 31.

Marshall et al., "Extraction of DNA from Malaria-Infected Erythrocytes Using Isotachophoresis." 2011, Analytical Chemistry, pp. 9715-9718.

McManus et al., "Circulating MicroRNAs in Cardiovascular Disease." Comment on Circulation. 124(18), Nov. 1, 2011, Comment on Circulation, pp. 1936-1944.

Mitchell et al., "Circulating microRNAs as stable blood-based markers for cancer detection." Jul. 29, 2008, PNAS, vol. 105, pp. 10513-10518.

Morales et al., "Continuous microfluidic DNA and protein trapping and concentration by balancing transverse electrokinetic forces." 2012, Lab Chip, pp. 99-108.

Qiao et al., "Wirelessly powered microfluidic electrophoresis devices using printable." 2011, Lab Chip, vol. 11, pp. 1074-1080.

Qu et al., "Circulating miRNAs: Promising Biomarkers of Human Cancer." 2011, Asian Pacific Journal of Cancer Prevention, vol. 12, 2011, pp. 1117-1125.

Shaikh et al., "Collection, focusing, and metering of DNA in microchannels using addressable electrode arrays for portable low-power bioanalysis." 2005, PNAS, 2006, pp. 4825-4830.

Shopova et al., "Plasmonic enhancement of a whispering-gallery-mode biosensor for single nanoparticle detection." 2011, Applied Physics Letters, pp. 243104-243104-3.

Suzuki et al., "Characterization of circulating DNA in healthy human plasma." Sep. 3, 2007, Clinica Chimica Acta, vol. 387, pp. 55-58.

Tamkovich et al., "Circulating Nucleic Acids in Blood of Healthy Male and Female Donors." Nov. 2004, Clinical Chemistry, vol. 51, pp. 1317-1319.

Th'Ery et al., "Isolation and Characterization of Exosomes from Cell Culture Supernatants." New York : John Wiley, 2006, Current Protocols in Cell Biology, pp. 3.22.1-29.

You et al., "Cell-phone-based measurement of TSH using Mie scatter optimized lateral flow assays." Biosensors and Bioelectronics, 2013, pp. 180-185.

Yu et al., "Circulating MicroRNAs: Potential Biomarkers for Cancer." 2011, Int. J. Mol. Sci., vol. 12, pp. 2055-2063.

Zhu et al., "Circulating microRNAs in breast cancer and healthy subjects." BioMed Central, 2009, vol. 2, p. 89.

Godin et al., "Microfluidics and photonics for Bio-System-on-a-chip: A review of advancements in technology towards a microfluidics flow cytometry chip." Journal of Biophotonics, 2008, pp. 355-376.

MicroRNAs in Blood May be Biomarkers of Pancreatic Cancer. NIH, News. Sep. 1, 2009, http://www.nih.gov/news/health/sep2009/nci-01.htm.

International Search Report and Written Opinion of International Application No. PCT/US2014/011942; dated Apr. 15, 2014; 12 pages.

International Search Report and Written Opinion of International Application No. PCT/US2014/011909; dated Dec. 9, 2014; 15 pages.

Mallick et al., "MicroRNAs and lung cancer: Biology and applications in diagnosis and prognosis." Aug. 3, 2010, J Carcinog, vol. 9.

\* cited by examiner

LABEL FREE MOLECULAR DETECTION METHODS, SYSTEMS AND DEVICES

CROSS REFERENCE TO RELATED APPLICATIONS

This patent document is a 35 USC §371 National Stage application of International Application No. PCT/US2014/011942 filed Jan. 16, 2014, which further claims the benefit of priority of U.S. Provisional Patent Application No. 61/753,384, entitled "LABEL FREE MOLECULAR DETECTION METHODS, SYSTEMS, AND DEVICES," filed on Jan. 16, 2013. The entire content of the aforementioned patent applications are incorporated by reference as part of the disclosure of this application.

TECHNICAL FIELD

This patent document relates to biological sensors and analytical devices.

BACKGROUND

A biological sensor or biosensor is an analytical tool that can detect a chemical, substance, or organism using a biologically sensitive component coupled with a transducing element to convert a detection event into a signal for processing and/or display. Biosensors can use biological materials as the biologically sensitive component, e.g., such as biomolecules including enzymes, antibodies, aptamers, peptides, nucleic acids, etc., or small molecules such as carbohydrates, as well as virus and living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by a suitable transduction mechanism, for example, electrical, magnetic, mechanical, physicochemical, electrochemical, optical, piezoelectric, or others.

SUMMARY

Techniques, systems, and devices are disclosed using molecular probes for on-chip, label-free, high-specificity and high-sensitivity detection of molecules from a fluid.

In one aspect, a method for capturing nucleic acids includes circulating a fluid containing nucleic acids through a microfluidic channel having a molecular probe attached to an interior surface of the channel, the molecular probe including a complimentary base pair region initially zipped in a hair-pinned structure, and a binding agent to chemically bind the molecular probe to an outer surface of a magnetic bead, applying a magnetic field having a magnetic field intensity across the microfluidic channel that interacts with the magnetic bead bound to the molecular probe to unzip the complementary base pair region to expose a base pair sequence complimentary to a nucleic acid base pair sequence, thereby enabling a circulating nucleic acid molecule to hybridize to the unzipped complementary base pair sequence of the molecular probe, and reducing the magnetic field intensity to promote the reforming of the hair-pinned structure for unhybridized molecular probes, e.g., while maintaining the hybridization of the nucleic acids to the molecular probes having the complementary base pair sequence.

In another aspect, a molecular probe device includes a molecular probe having a complimentary base pair region initially zipped in a hair-pinned structure and structured to include a binding agent to chemically bind the molecular probe to an outer surface of a magnetic bead, and a binding molecule to chemically bind the molecular probe to a surface, in which the complimentary base pair region is configured to hybridize to a complementary nucleic acid sequence of a DNA or RNA molecule.

In another aspect, a device to capture, enrich, and detect biomolecules from a fluid includes a substrate formed of a material that is electrically insulating, a microfluidic channel made of an electrically insulating material formed on the substrate to carry a biofluid containing nucleic acids, an array of electrodes formed on the surface along a parallel direction of the microfluidic channel constituting a capture region, in which the array of electrodes are operable to produce an electric field across the microfluidic channel that creates an electrostatic attractive force on the nucleic acids to immobilize them in the capture region, a chamber formed on the substrate of the electrically insulating material and connected to the microfluidic channel, the chamber configured to have a volume less than that of the microfluidic channel, such that, when the nucleic acids are released from immobilization in the capture region, the released nucleic acids are collected in the chamber at a higher concentration than that in the capture region, and a plurality of molecular probes attached to the substrate in the chamber, the molecular probes structured to include a single stranded DNA oligo having a complimentary base pair region initially zipped in a hair-pinned structure, a magnetic bead attached to one end of the single stranded DNA oligo via a binding agent, and a binding molecule to chemically attach the molecular probe to the substrate in the chamber, in which the complimentary base pair region is configured to hybridize to a complementary nucleic acid sequence of a target DNA or RNA molecule.

The subject matter described in this patent document can be implemented in specific ways that provide one or more of the following features. For example, the disclosed molecular probes can be tethered to transparent iron oxide magnetic beads and operable to produce optical signatures associated with a change in length of the probes after hybridizing with the target molecule (e.g., nucleic acids). For example, the disclosed technology provides a platform that can be applied to most or all types of miRNAs (e.g., nearly 2000 mature human miRNAs have been found and profiled for disease diagnosis) and in a variety of clinical oncology applications. Exemplary applications include early detection of cancer, e.g., such as non-small-cell lung cancer (NSCLC), which is difficult to diagnosis otherwise. The disclosed detection techniques are minimally invasive as compared to the current methods. In some aspects, the disclosed technology can function as the back-end detection component of a lab-on-a-chip miRNA diagnostic device or research tool.

DETAILED DESCRIPTION

Figure 1A:
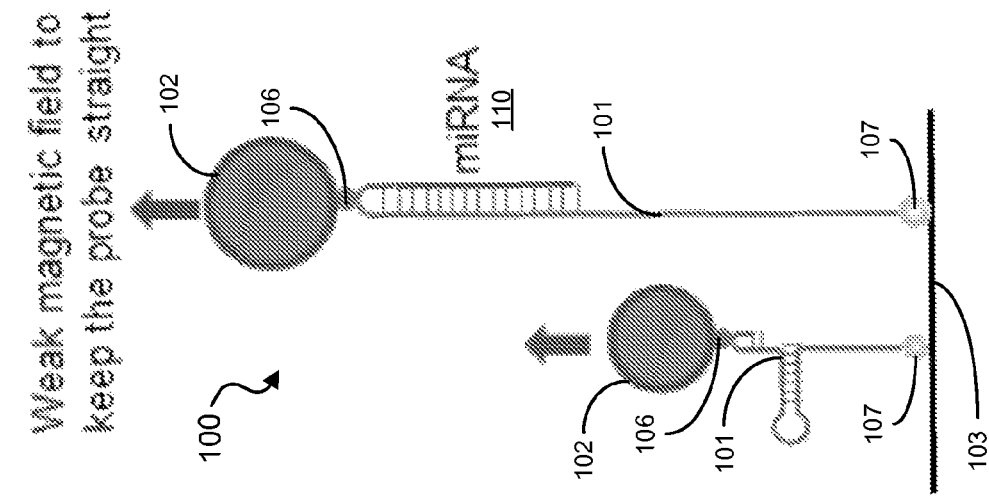
FIGS. 1A-1C show a series of schematic illustrations of exemplary molecular probes of a molecular detection device of the disclosed technology for controlled binding with a target nucleic acid under an applied magnetic field.

Nucleic acids are polymeric biological molecules that are considered essential for all known forms of life. Nucleic acids include deoxyribonucleic acid (DNA) and ribonucleic acid (RNA), which are formed from particular arrangements of monomer subunit molecules called nucleotides. Nucleotides are composed of a nitrogenous base, a five-carbon sugar (e.g., deoxyribose if the polymeric biomolecule is DNA, or ribose if the polymeric biomolecule is RNA), and at least one phosphate group. There are many subtypes and chemical modifications of nucleic acids that serve one or more functions in the genetic make-up of living and non-living organisms.

For example, microRNAs (miRNAs) are small non-coding RNA molecules of about 21 to 23 nucleotides in length, which function in the regulation of gene expression. Over 2,000 types of mature miRNAs have been found to date, and new miRNAs continue to be discovered by research laboratories around the world. Because miRNAs are linked to over 100 diseases, including many types of cancers, they can be used as biomarkers for disease diagnosis. Furthermore, circulating miRNAs, either secreted by diseased tissues or produced due to immune responses, exist in blood and biofluids, so they are particularly promising for early disease diagnosis with minimal invasiveness.

Currently, many technical challenges exist to measure many miRNAs, e.g., as some miRNAs differ from each other by one or a few nucleotides and link the levels to various disease conditions. There are significant research efforts being made in connecting miRNAs to specific diseases, e.g., particularly with circulating miRNAs, establishing amongst those in the medical community that miRNAs will become important biomarkers, in addition to proteins and DNAs, for diagnosis of a large number of diseases including, e.g., cancers, chronic diseases, immune diseases, etc. However, the medical community lacks devices for miRNA-based assays that are suitable for clinical applications, e.g., which can create a major bottleneck to translate the fast discoveries of miRNAs in the laboratories to the clinics.

Currently, any clinical miRNA detection technology using blood or biofluids face the challenge of very low concentrations of specific miRNAs and the time and cost of detection since accurate test results need to be produced fast and at low cost. For example, the level of specific miRNAs in blood or another biofluid such as saliva can be as low as 10 femtomolar (fM). For reliable detection of miRNAs or other biomolecules in practical settings, e.g., such as a point-of-care diagnosis, one may need to rapidly collect about 1-10 attomoles ($10^{-17-18}$ moles) of the target nucleic acids (e.g., miRNAs) from about 1 mL of blood. Under these exemplary conditions, to extract and concentrate enough amounts of miRNAs in less than 30 minutes, a flow rate of 30-100 µL/min would needed at decent collection efficiency (e.g., >10%), which is well beyond the capabilities of any existing/conventional microfluidic nucleic acid extraction devices. One alternative is to collect miRNAs encapsulated in exosomes, but the steps required to collect exosomes (e.g., ultra centrifuge at 100,000 gs or using CD63 antibody) can add extra time, cost and process complexity (e.g., 4-5 hours for 5-25% exosome collection efficiency). Therefore, free miRNAs directly from blood or biofluids can be chosen to be collected.

Techniques, systems, and devices are disclosed using molecular probes for on-chip, label-free, high-specificity and high-sensitivity detection of molecules from biological fluids (e.g., including nucleic acids, such as miRNA). The disclosed molecular probes enable label-free optical detection of single miRNA binding events on a low-cost, lab-on-a-chip platform with high specificity and high sensitivity. In some implementations, for example, an exemplary molecular probe can include a hair-pinned molecular probes tethered to transparent iron oxide magnetic beads, and optical signatures associated with a change in length of the probes after hybridizing with the miRNAs.

In some aspects, methods and devices to achieve on-chip, label-free, high-sensitivity miRNA detection using a hair-pinned molecular probe tethered to a transparent iron oxide magnetic bead are described. In some implementations, the probe can be configured as a custom synthesized DNA oligo, and the hairpin structure is formed in the middle with two 15 bp stems that are complementary to each other and to a specific nucleic acid sequence (e.g., miRNA sequence). For example, when an appropriate magnetic force is applied, the stem in the middle of the probe is unzipped and the target miRNA can hybridize with the probe. After binding with the target miRNA, for example, the linear length of the probe is increased, e.g., by 12-14 nm, which can be detected optically. In some implementations, detection can be performed using a red diode laser coupled to a SiN waveguide on glass substrate, e.g., in which the light couples to the magnetic beads which then produce radiation with a signature far-field pattern that changes in intensity when the distance between the bead and the waveguide becomes longer due to the binding with target miRNAs. Such intensity change can be clearly detected by existing CCD or CMOS camera technology. For example, the unique sequence of the miRNA in the 15 bp stem region is used to maximize the specificity of the probe and reduce the stability of it binding to a similar miRNA, e.g., based on energy calculations. In some implementations, for example, different types of molecular probes can be placed in separate areas (e.g., about 500×500 µm²  each) in the detection section of a lab-on-a-chip device. The disclosed technology can function as the back-end detection component of a lab-on-a-chip miRNA diagnostic device, e.g., which can be included in combination with the front-end miRNA capture/release component of an exemplary microfluidic device disclosed herein.

In one aspect, a molecular detection device of the disclosed technology includes a molecular probe having a complimentary base pair region initially zipped in a hair-pinned structure and including a binding agent to chemically attach the molecular probe to an outer surface of a magnetic bead, in which the complimentary base pair region is configured to hybridize to a complementary nucleic acid sequence of a DNA or RNA strand, e.g., such as an miRNA sequence of an miRNA molecule. The molecular detection device includes a binding molecule to chemically attach the molecular probe to a substrate (e.g., such as a substrate of a microfluidic device).

In some implementations of the molecular detection device, for example, the surface of the substrate can be coated with anti-digoxigenin antibody and the binding molecule can be digoxigenin. In some implementations, for example, the binding agent can include biotin, and the magnetic bead can include a streptavidin-coated outer surface. For example, the molecular probe can be configured to have a short length that disfavors binding with longer RNA molecules. For example, the molecular probe can be structured to prohibit interaction with circulating double stranded nucleic acids. For example, the exemplary molecular probe is operable to interact with an applied magnetic field via the magnetic bead such that the magnetic field attracts the magnetic bead to move and thereby unzip the complementary base pair region to expose a base pair sequence complimentary to a base pair sequence of a target nucleic acid, and, when unzipped and exposed to the target nucleic acid, hybridize the complimentary base pair sequence to the base pair sequence of the target nucleic acid. For example, the molecular probe can be configured to resist the unzipping of the hybridized base pair sequence with the target nucleic acid when the magnetic field intensity is reduced. For example, the molecular probe is further operable to re-form to the hair-pinned structure if the unzipped complementary base pair region is not hybridized to the base pair sequence of the target nucleic acid and the magnetic field intensity is reduced.

In some implementations, for example, the molecular probe can include a fluorophore to emit a fluorescent signal upon optical actuation. In the exemplary cases in which the fluorophore is implemented in the molecular detection device, the fluorophore molecule can be linked to the end of the molecular probe near or as part of the binding agent. In such cases, the magnetic bead may not be employed on the molecular probe. For example, without hybridization of the target nucleic acid (e.g., such as miRNA), the molecular probe is in its initial state and the fluorophore molecule would be relatively close to the surface of the substrate (e.g., where a layer of gold may be deposited). Due to the close distance (e.g., <3 nm) between the fluorophore and gold layer, the fluorescence is quenched. However, after hybridization with the target nucleic acid, the distance between the fluorophore and gold is separated by a greater distance (e.g., around 10 nm), and the quenching effect would disappear and the fluorescence can be detected.

FIG. 1A shows a schematic illustration of an exemplary molecular detection device 100 to detect a target nucleic acid, e.g., miRNA 110, in a manner that can be employed on a lab-on-a-chip device, label-free, and with high-sensitivity. As shown in the diagram, the device 100 includes multiple hair-pinned molecular probes 101 tethered to a magnetic bead 102. The molecular probes 101 can be attached to a surface of the detection area of an exemplary lab-on-a-chip device. In the example shown in FIG. 1A, the molecular probes 101 are attached to a substrate 103 in a microfluidic channel or chamber of a lab-on-a-chip device. The molecular detection device 100 can be configured of multiple types of molecular probes 101 to detect multiple types of nucleic acids. For example, since the expression levels of two or more circulating miRNAs (e.g. miR-155, miR-197, and miR-182) can be measured by the device 100, each type of the molecular probes 101 can be deposited in specific areas on the surface 103 of the lab-on-a-chip device (e.g., in areas of about 0.5×0.5 mm$^2$ each).

As shown in FIG. 1A, the molecular probe 101 is configured as a custom synthesized DNA oligo with an internally labeled biotin 106 at a 5' end stem-loop structure to attach the DNA oligo portion of the probe 101 to the magnetic bead 102. The DNA oligo portion of the probe 101 is attached to the substrate 103 at the 3' end by a digoxigenin 107. In this example, the biotin structure 106 attaches the oligo to a streptavidin coated magnetic bead 102, while the digoxigenin 107 anchors the probe 101 to an exemplary glass surface coated with anti-digoxigenin antibody. The hairpin structure in the middle of the molecular probe 101 body is configured with two multi-base pair stem portions complementary to each other and to a specific nucleic acid sequence (e.g., miRNA sequence). In the example shown in FIG. 1A, the hairpin structure of the molecular probes 101 include two exemplary 15 base pair (e.g., 15 bp) stem portions complementary to each other and to a specific miRNA sequence of the miRNA 110.

For example, when an appropriate magnetic force is applied, the stem portions of the probes 101 complementary to each other become unzipped and the target nucleic acids (e.g., miRNA 110) can hybridize with the probe 101 at the unzipped base pairs. For example, when the magnetic force is reduced, a hybridized probe will not be able to re-form the hairpin structure as an unhybridized probe will. After the binding with the target miRNA 110, the linear length of the probe is increased by 12 to 14 nm, in this example, which can be detected optically, as described below. The molecular probe 101 has a short length that disfavors binding with long RNAs. The molecular probes 101 of the device 100 can also interact minimally with circulating ds-DNAs and si-RNAs that are double strained.

Figure 1B:
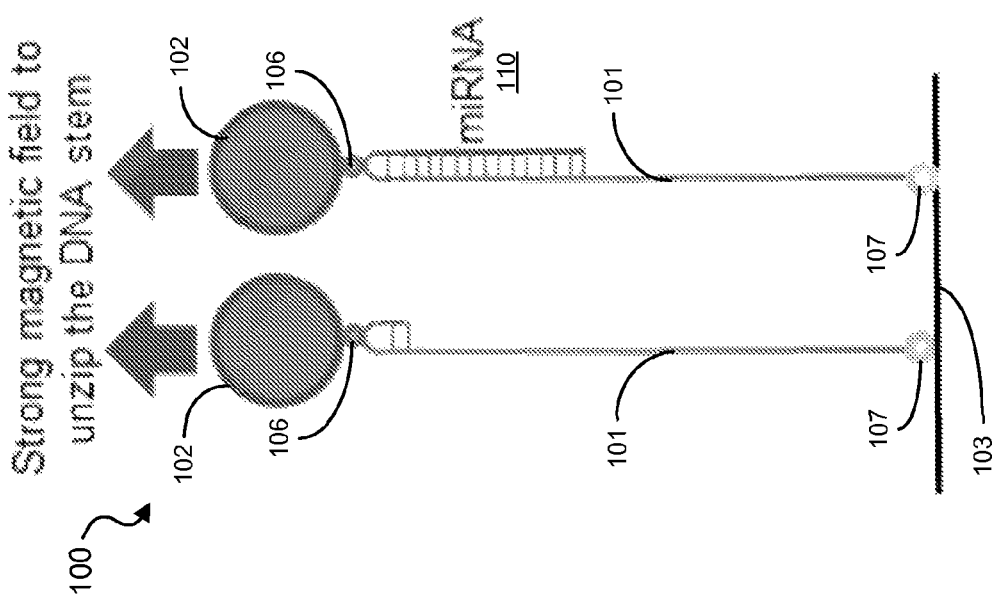
Figure 1C:
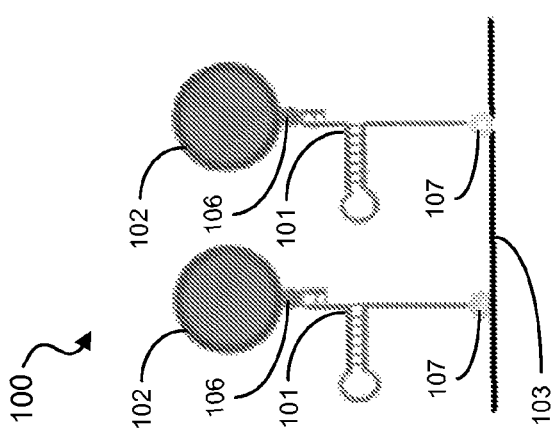

FIGS. 1A-1C show a series of schematic illustrations of the exemplary molecular detection device 100 for controlled binding with a target nucleic acid (e.g., miRNA 110) under an applied magnetic field. In the exemplary illustrations, the distance of the magnetic bead 102 to the exemplary glass surface 103 changes due to specific binding of the miRNA 110 to the complementary nucleic acid sequence of the molecular probe 101. The height difference can be detected optically. FIG. 1B shows the exemplary scenario where a strong magnetic field is applied to the detection device 100 to unzip the stem portions of the molecular probes 101 complementary to each other to present the base pair region complementary to a specific miRNA sequence to bind the miRNA 110. FIG. 1C shows the exemplary scenario where a weak magnetic field is applied to the detection device 100 to keep the molecular probe 101 that has detected the target miRNA 110 straight while allowing any unbound molecular probes to return to their initial configurations.

Exemplary implementations using the molecular detection device 100 on a substrate to detect miRNA were performed. In the exemplary implementations, the molecular probes used had a 5' stem-loop structure with a biotin structure to anchor the probe to the magnetic bead, a hairpin structure close to the middle of the molecular probe body, and a 3' end with digoxigenin to attach to the substrate. For example, the biotin was bound to 1 μm diameter iron oxide magnetic beads coated with streptavidin, and the digoxigenin was attached to a glass slide surface coated with an anti-digoxigenin antibody. The oligo DNAs used in the exemplary implementations were custom synthesized by IDT DNA technology. For example, the 5' stem-loop design allows only mature miRNA to bind, e.g., preventing premiRNA and other large RNA or DNA from binding because of steric hindrance. The hairpin in the middle contained two 15 bp of sequences complementary to each other and to a specific miRNA sequence, which formed a stem. During the exemplary implementations, when an appropriate magnetic force was applied, the stem in the middle of the probe was unzipped so that the miRNA in the fluid could hybridize with complementary region on the probe. The unique sequence of the miRNA in the 15 bp stem region can be used to maximize the specificity of the probe and reduce the stability of the probe binding to a similar miRNA based on energy calculation of the complex.

Figure 2A:
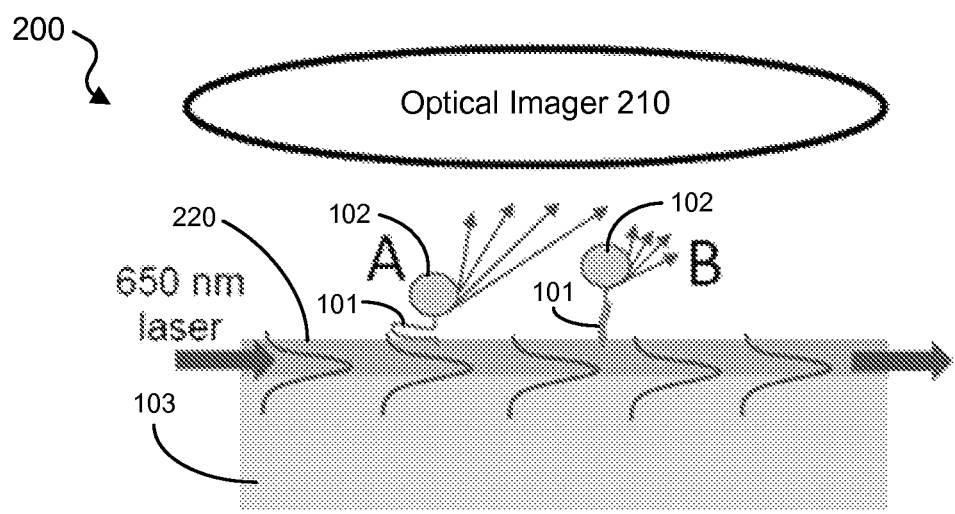
FIGS. 2A and 2B show diagrams including schematic illustrations and micrographs of optical detection by exemplary molecular probes with and without bonding to a target miRNA.

A method for capturing nucleic acids includes circulating a fluid containing nucleic acids (e.g., such as miRNA molecules) through a microfluidic channel of a lab-on-a-chip device, in which the device includes a detection region having the molecular detection device 100. For example, the molecular probes 101 can be attached to an interior surface in the microfluidic channel or a chamber of the lab-on-a-chip device and bound to the magnetic bead 102 at the other end of the probe 101. The method can include applying a magnetic field having a magnetic field intensity across the microfluidic channel that interacts with the magnetic bead 102 bound to the molecular probe 101 (e.g., which attracts the magnetic bead to move in a direction away from the interior surface of the channel) to unzip the complementary base pair region of the hairpin structure of the probes 101 to expose a base pair sequence complimentary to a nucleic acid base pair sequence, thereby enabling a circulating nucleic acid (e.g., miRNA) molecule to hybridize to the unzipped complementary base pair sequence of the molecular probe. The method can include reducing the magnetic field intensity to promote the reforming of the hair-pinned structure for unhybridized molecular probes, e.g., while maintaining the hybridization of the nucleic acids to the molecular probes having the complementary base pair sequence The detection of the binding events of target miRNAs optically can be implemented. For example, at first a strong enough magnetic field is applied to the magnetic beads (e.g., exemplary iron-oxide magnetic beads) to unzip the stem of the hairpin of the probes 101, and thus exposing the single-stranded DNA to the target miRNAs. When the surrounding miRNAs find the matched section of the DNA probe and form the DNA/miRNA duplex, the hairpin can no longer be formed after the removal of the external magnetic field, unlike those free probes where the hairpin is restored once the magnetic field is removed. Next, for example, a weak magnetic field is applied to keep all probes standing tall (e.g., as depicted in the diagram of FIG. 2A showing two exemplary magnetic beads A and B connected to respective molecular probes). Because such weak magnetic force is insufficient for unzipping the stem of the hairpin, the distance between the exemplary iron-oxide bead and the substrate differs (e.g., by 12-14 nm) for probes that bind the target nucleic acids and those that do not.

Figure 2B:
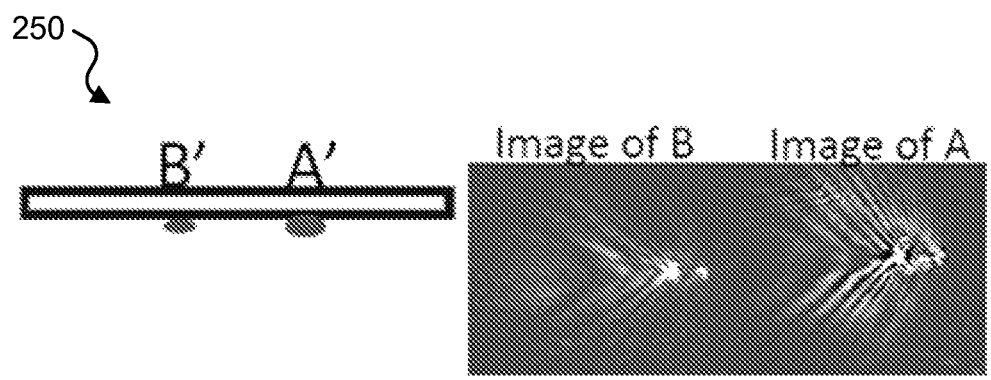

FIGS. 2A and 2B show diagrams including schematic illustrations and micrographs of optical detection by exemplary molecular probes with and without bonding to a target miRNA. For example, to detect such a distance difference optically, a red diode laser (e.g., $\lambda$=650 nm) is coupled to a SiN waveguide (e.g., n=2.0) on glass substrate (e.g., n=1.42). The light is evanescently coupled, through the water medium (e.g., n=1.33) to the transparent iron oxide magnetic bead that also functions as an optical resonator or a scattering center. The iron-oxide bead (e.g., 1 µm in diameter and transparent to red light), behaving as a leaky optical resonator, receives the photon energy from the waveguide and produces radiation with a signature far-field pattern. When the distance between the bead and the waveguide becomes longer, e.g., 12 to 14 nm longer in this example, due to the binding with target miRNAs, the optical coupling strength is substantially reduced, e.g., by 30-50% in some exemplary implementations. Such intensity change can be clearly detected by exemplary optical imagers, e.g., CCD or CMOS cameras mounted to a microscope. Diagram 200 of FIG. 2A shows an exemplary setup of the optical detection system including the molecular detection device 100 on a substrate including a waveguide 220 and an optical imager 210. The diagram depicts exemplary iron-oxide magnetic beads 102 for probes A and B, in which miRNA is bonded to the probe B. Diagram 250 of FIG. 2B an illustration of the optical output of the probes A and B (represented as probes A' and B') produced by the optical imager 210. FIG. 2B also shows micrograph images of the exemplary probes A and B depicting their different scattering intensities and patterns.

Figure 2C:
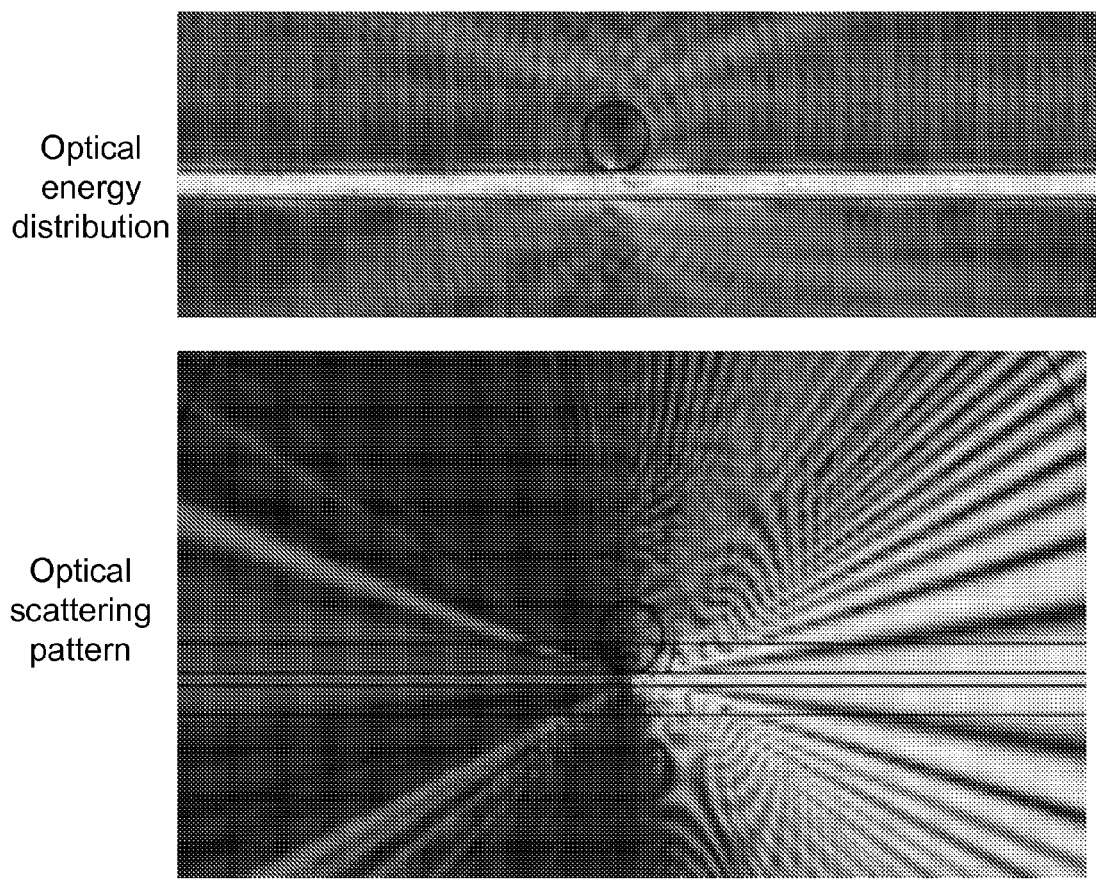
FIG. 2C shows images of the optical energy distribution and optical scattering pattern by an exemplary 1 µm diameter iron-oxide magnetic bead of exemplary molecular probes near a SiN waveguide.

FIG. 2C shows images of the optical energy distribution (upper image) and the optical scattering pattern (lower image) by an exemplary 1 µm diameter iron-oxide magnetic bead of the molecular probes near a SiN waveguide. The exemplary images of FIG. 2C represent simulated optical energy density (upper) and scattering pattern (lower) of a spherical bead. For example, because binding of target miRNA reduces the scattering signal, software (e.g., ImageJ) was used to count the dimmed spots, which are related to the concentration of specific miRNAs. The binding kinetics of miRNAs can be measured. The rate of change in the scattering pattern also provides information about the concentration of target miRNAs.

In some implementations, each critical step of miRNA detection can include a contingency procedure. For example, provided the optical scattering does not produce enough signal-to-noise ratio to unequivocally determine the binding event, the magnetic field can be modulated to transiently move the position of magnetic beads and monitor the temporal response of beads with and without miRNA binding. In this exemplary procedure, the measurement may take longer and require more signal processing but the sensitivity will be increased. If non-specific binding of miRNA occurs, a gradually increase of the temperature can be implemented to detect the temperature dependent signals which give information about specific and non-specific binding.

For example, each type of molecular probes can be placed in separate areas (e.g., about 500×500 µm$^2$ each) in a capture region of a lab-on-a-chip device. Examples of the disclosed systems and lab-on-a-chip devices that can employ the disclosed molecular detection devices are provided in PCT Patent Application PCT/US14/11909, entitled "MICROFLUIDIC DEVICES TO EXTRACT, CONCENTRATE AND ISOLATE MOLECULES," filed Jan. 16, 2014, of which the entire contents are incorporated by reference for all purposes as part of the disclosure of this patent document.

Figure 3:
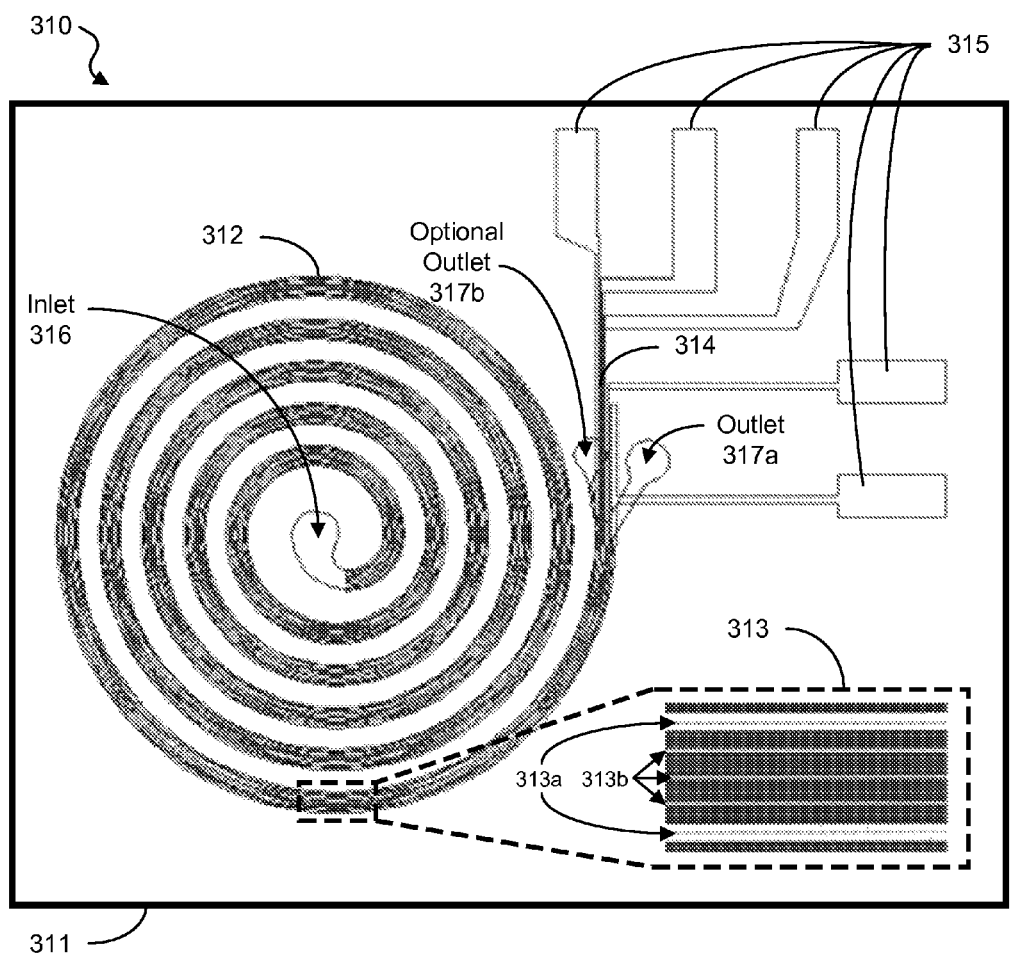
FIG. 3 shows a schematic illustration of an exemplary lab-on-a-chip device to capture, enrich, and/or detect target molecules from a fluid.

In one exemplary embodiment, a lab-on-a-chip device for capture, release, and detection of molecules including nucleic acids such as DNA and miRNA using the disclosed molecular detection technology is shown in FIG. 3. FIG. 3 shows a schematic illustration of an exemplary device 310 to capture, enrich, and/or detect target molecules from a fluid. For example, the fluid can include biofluids including, e.g., blood, saliva, sputum, urine, vitriol fluid, and/or other fluid derived from an organism. The device 310 includes electric field assisted capture and release functionalities. In some implementations, for example, the device 310 can be used to capture nucleic acids (e.g., DNA or RNA, such as miRNA) contained in the blood that are at a concentration in a femtomolar range or less for enrichment. Subsequently, for example, the device 310 can be implemented to transfer the enriched nucleic acids to a detection region including a plurality of molecular probes 101 of the molecular detection device 100 for optical detection and characterization of the enriched nucleic acids.

The device 310 includes a substrate 311 formed of a material that is electrically insulating. In some implementations, for example, the substrate 311 can be formed of glass, oxidized silica, cyclic olefin copolymer, polycarbonate, polyethylene, or other substrate including an electrically insulating coating or surface. The device 310 includes a microfluidic channel 312 made of an electrically insulating material (e.g., such as polydimethylsiloxane (PDMS)) formed on the substrate 311 to carry a fluid (e.g., biofluid) containing molecules, e.g., such as nucleic acids. The device 310 includes an array of electrodes 313 formed on a surface within the microfluidic channel 312 along a parallel direction of the microfluidic channel, e.g., constituting a capture region of the device 310. The array of electrodes 313 are operable to produce an electric field across the microfluidic channel 312 that can create an electrostatic attractive force on the molecules (e.g., nucleic acids) to immobilize them within the capture region of the device 310. The device 310 can include an inlet 316 to receive the fluid, e.g., which can be a raw sample or a conditioned sample. The device 310 can include one or more outlets 317 (e.g., depicted in FIG. 3 as outlet 317a and optional outlet 317b) for removing the sample fluid after flowing through the capture region. For example, a plurality of outlets 317 can be used to control the flow rate of the sample fluid through the device 310.

The device 310 includes a microchamber 314 formed on the substrate 311 at the end of the microfluidic channel 312 to receive the captured molecules after they are released from the capture region and recapture the released molecules, e.g., thereby constituting a recapture region of the device 310. For example, the microchamber 314 can be configured to have an area and/or volume substantially smaller than the microfluidic channel 312 to provide a section of the device to collect, enrich and increase the concentration of the captured molecules by the device 310. For example, in some implementations, the microfluidic channel 312 (capture region) can be configured to have a volume in the microliter range (e.g., ~5 µL), whereas the microchamber 314 can be configured to have a volume in the nanoliter range (e.g., ~10 to 100 nL). In some implementations, for example, the microchamber 314 provides a detection region of the device 310 for electrical and/or optical detection of the enriched recaptured molecules within the chamber 314. For example, in some implementations, the microchamber 314 can include the molecular probe devices 100 capable of binding the target nucleic acid molecules in the chamber 114 for detection.

In some embodiments, for example, the device 310 can further include one or more detection regions or chambers 315 formed on the substrate 311 to provide optical detection for characterization (e.g., including quantification) of the presence, concentration, and/or properties of the enriched molecules. The one or more detection regions 315 can be structured to include a plurality of the molecular probes 101 (with attached magnetic beads 102) anchored to the substrate 311 in the detection region(s) 315. For example, the substrate surface in the detection region 315 can be modified with a coating of an anti-digoxigenin antibody for binding the molecular probes 101 via a digoxigenin complex. The plurality of molecular probes 101 can be configured in multiple sections of the detection region 315 for detection of multiple corresponding target molecules based on the hairpin structure (e.g., complementary base pair sequence) in the molecular probe groupings.

The device 310 can be operated to enrich molecules from the fluid as follows. For example, the immobilized molecules (e.g., nucleic acids) can be released from the capture region by implementing at least one of the following exemplary processes. In one exemplary process, the device 310 can be operated to remove or reduce the applied electric field (and thereby release the immobilized molecules from the capture region) while flowing another fluid to fluidically transfer the released molecules to the recapture region 314 of the device 310. In another exemplary process, the device 310 can be operated to receive a buffer fluid capable of changing the pH of the fluidic environment of the capture region, and thereby altering the attractive force of the applied electric field to release the release the immobilized molecules from the capture region.

In some implementations of the device 310, for example, the microfluidic channel 312 (in the capture region) can be configured as a spiral-shaped channel. For example, the exemplary spiral shaped microfluidic channel 312 can be configured to have a length of at least 40 cm and a diameter of 4 cm or less. In other implementations, for example, the microfluidic channel 312 can be configured as a straight channel in another geometry on the substrate 311. The exemplary embodiment shown in FIG. 3 depicts the spiral geometry of the capture region of the microfluidic device 310. The arrayed electrodes 313 are configured along the spiral-shaped channel 312. This exemplary embodiment can be configured to have a large effective channel length (e.g., of over 40 cm) in spite of its compact size (e.g., 4 cm diameter).

The inset of FIG. 3 shows a diagram of an exemplary configuration of the array of electrodes 313 of the device 310. In this example, the array of electrodes 313 includes two peripheral electrodes 313a and interior electrodes 313b arranged along the direction of the microfluidic channel 312. The peripheral electrodes 313a are arranged on the outlying portion of the channel surface and are structured to include a larger width (e.g., 300 µm to 1 mm) than interior electrodes 313b (e.g., which may range from 10 µm to 30 µm). In some examples, the electrodes of the array 313 can be configured of gold, platinum, or other metallic material having good electric conductivity and noncorrosive properties. In some implementations, the electrodes 313 can be functionalized to attach molecules or molecular structures, e.g., including targeting ligands to assist in binding the target molecules to the capture region of the microfluidic channel 312.

For example, the device 310 can use electrophoretic and/or dielectrophoretic forces to enable selective capturing of biomolecules in the capture region based on the characteristic frequency response of the dielectric permittivity of the biomolecule versus that of the medium. In some implementations, for example, an external circuit or electrical supply source can be electrically coupled to the array of electrodes 313 to provide an electrical signal and power to the device 310. For example, in some implementations, a DC electrical potential can be applied across the peripheral electrodes 313a parallel along the microfluidic channel 312 to produce an DC electric field. For example, because the device 310 can be operated at a high flow rate (e.g., 30 µL/min or greater), the applied DC potential can be greater than the high threshold of hydrolysis of 0.82 $V_{DC}$ (e.g., 2 $V_{DC}$), as the applied electrical field would not damage the nucleic acids during implementation. In some implementations, for example, an AC electrical potential can be applied across the peripheral electrodes 313a parallel along the microfluidic channel 312 to produce an AC electric field. For example, the applied AC electric field may cause a negative dielectrophoretic effect in high electrolytic solutions to provide the molecular capture force of the exemplary nucleic acids in the capture region. In some implementations, for example, both an AC electric potential with a DC bias may be applied. In some configurations, for example, the interior electrodes 313b are not directly connected to an external circuit, and rather function to bend or shape the electric field produced by the applied electrical potential on the peripheral parallel electrodes 313a. Yet in some configurations, for example, each of the interior electrodes 313b can be connected to the external circuit so that their voltage value or waveform can be independently controlled and set.

In some implementations of the device 310, the exemplary biofluids is flowed through the microfluidic channel 312 at a flow rate of 30 µL/min or less. In some implementations of the device 310, for example, the substrate 311 can further include silica beads configured on the surface of the substrate 311 within the microfluidic channel 312, in which the silica beads provide a negative surface charge used to attract and bind the nucleic acids having a net positive charge. In other implementations of the device 310, for example, the substrate 311 can further include silica beads configured on the surface of the substrate 311 within the microfluidic channel 312, in which the silica beads provide a positive surface charge used to attract and bind the nucleic acids having a net negative charge.

Figure 4:
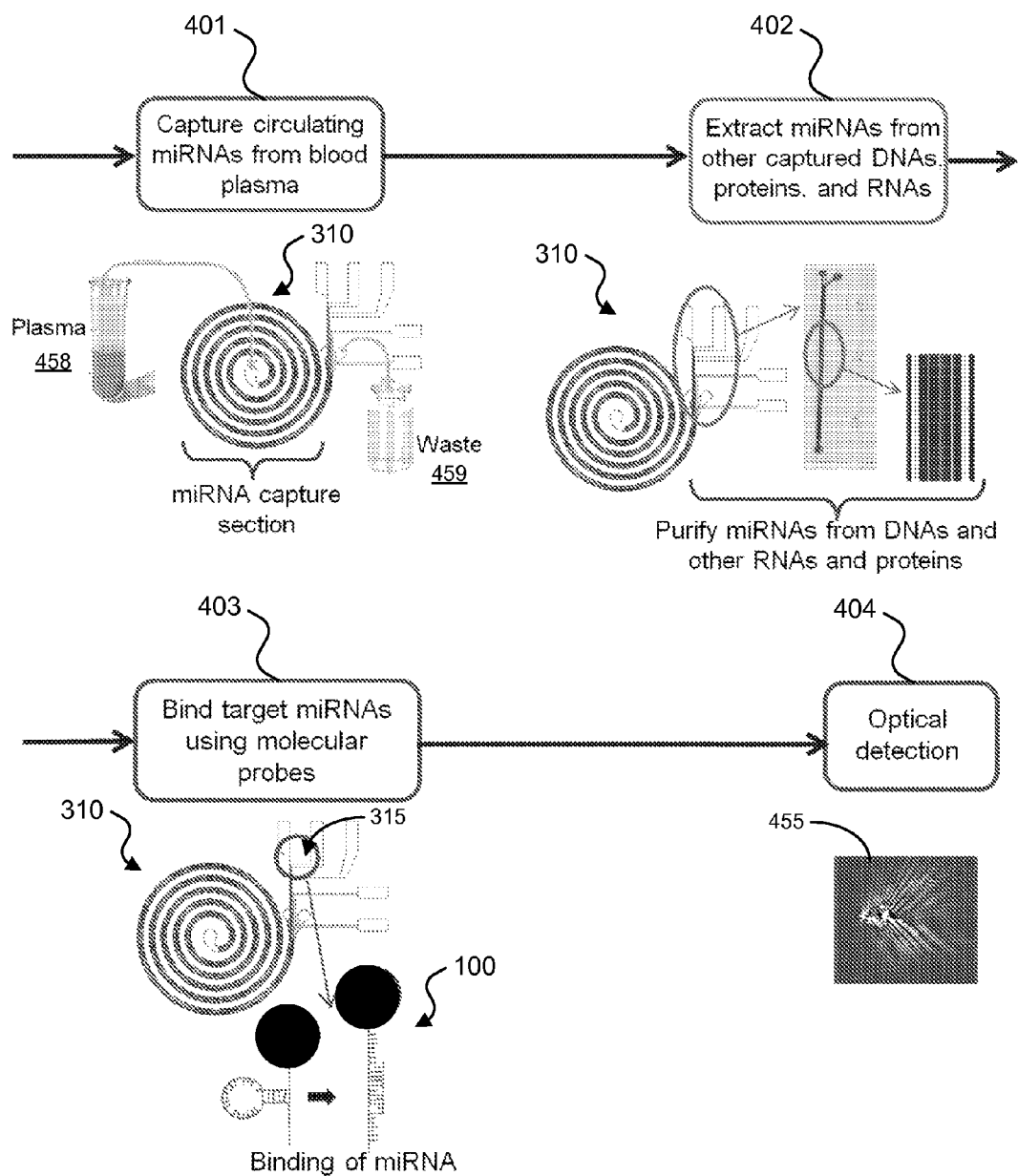
FIG. 4 shows an illustrative diagram of the process flow of the exemplary lab-on-a-chip device of FIG. 3 for capture, extraction and enrichment, and detection of nucleic acid molecules from a biofluid using the disclosed molecular probe technology.

FIG. 4 shows an illustrative diagram of the process flow of the exemplary lab-on-a-chip device 310 implemented to capture, extract and enrich, and detect miRNA molecules from blood plasma using the disclosed molecular probe technology.

As shown in the diagram, a process 401 can be performed to capture circulating miRNAs from blood plasma or whole blood received by the device 310 (e.g., via the inlet 316) from a sample vial or container 458. In the flow direction of the blood plasma, the array of electrodes 313 formed in parallel with the microfluidic channel 312 are operated to electrophoretically capture miRNAs as they travel through the channel. For example, since miRNAs carry negative charge (e.g., about 23 electron charge for a 20 nt miRNA that is about 7 nm long), they can be attracted to the positive electrodes within the capture section of the device 310. Those captured miRNAs can be released from the capture section and recaptured in the microchamber 314 recapture section, e.g., having a much smaller volume than that of the capture section (e.g., 5 µL for the capture region as compared to 50 nL of the recapture region).

A process 402 can be performed to extract and enrich the miRNAs from other captured DNAs, proteins, and RNAs, etc., e.g., by purifying miRNAs from DNAs, RNAs, proteins and other biomolecules. For example, the process 402 can be implemented to apply an electric field to capture the miRNAs from the other types of nucleic acids, proteins, and other biomolecules based on the parameters of the applied electric field and properties of the miRNAs (e.g., zeta potential) that would cause capture of only the miRNAs.

In some implementations, for example, the recapture section can include the molecular detection probe devices 100 to detect the enriched miRNAs in the microchamber 314 recapture region, or can control the amount of miRNAs that can be released to the exemplary third section for detection (e.g., detection region 315) that includes the molecular detection probe devices 100. For example, in some implementations, the microchamber 314 can be configured to include one or more electrodes (e.g., such as in the array of electrodes 313), which can be operated to produce an electric field in the microchamber 314 to create an electrostatic attractive force on the released miRNAs (released from the capture region) that are transferred to the microchamber 314 for recapture in the recapture region. The molecular probe devices 100 can be functionalized to the surface of the substrate 311 in the detection region 315, where the extracted and enriched miRNAs can be transferred.

A process 403 can be performed in the detection region 315 of the device 310 to bind the target nucleic acids to the to the molecular probes 101 having the corresponding complementary base pair sequences, as exemplified in FIGS. 1A-1C. A process 404 can be performed to optically detect the specific binding events of target miRNAs to the molecular probes 101, as exemplified in FIGS. 2A-2C. For example, a micrograph 455 depicts an exemplary optical scattering signal signifying a single binding event.

Exemplary microfluidic lab-on-a-chip devices were developed with a magnetic enabled molecular probe to detect miRNAs captured in the previous stage. The exemplary design can transform the miRNA hybridization event into optical signal output. As a result, one can detect those targeted miRNAs without amplification step like RT-PCR. All these processes can be performed on a single lab-on-a-chip device, e.g., to simplify and streamline the process of miRNA-based rapid diagnosis.

Among the over 2,000 types of mature miRNAs known, some 88 miRNAs have been reported to show different expression levels in non-small cell lung cancer (NSCLC) patients. For example, the combination of three circulating miRNAs (e.g., miR-155, miR-197, and miR-182) are quite unique to NSCLC. Exemplary implementations of these microfluidic lab-on-a-chip devices can be performed using blood samples from healthy donors and NSCLC patients. to obtain an expression profile of three miRNA panel (e.g., miR-155, miR-197, and miR-182) associated with lung cancer, in which the miRNA signature obtained by the exemplary lab-on-a-chip devices can be compared with exemplary result from conventional real-time PCR method. Such implementations are illustrated with the example of non-small-cell lung cancer, yet the disclosed technology and methodology can also be applied to many other cancer and diseases and facilitate the translation of miRNA discovery into the clinic. The disclosed technology is suitable for point-of-care clinical applications.

Exemplary miRNA results of the exemplary devices can be compared and calibrated with the results from conventional RT-PRC. For example, an RNA isolation kit can be used to isolate miRNAs from 0.5 mL of serum from each individual and convert 3 µL of miRNAs (e.g., 2-5 ng) to cDNAs by reverse transcription using Megaplex Primer Pool. The cDNA then can be diluted with Taqman Universal PCR Master Mix and loaded into Taqman microRNA array plates or measured by individual Taqman miRNA assays. Based on the levels of miRNA revealed by PCR methods, the setting for the exemplary devices can be adjusted and measure each miRNA in the same samples.

Exemplary contingency procedures for each critical step of miRNA detection is included in the exemplary methods. For example, provided the optical scattering does not produce enough signal-to-noise ratio to unequivocally determine the binding event, the magnetic field can be modulated to transiently move the position of magnetic beads and monitor the temporal response of beads with and without miRNA binding. In this exemplary process, the measurement may take longer and require more signal processing, but the sensitivity will be increased. If non-specific binding of miRNA occurs, a gradual increase of the temperature can be implemented to detect the temperature dependent signals which give information about specific and non-specific binding.

Figure 5:
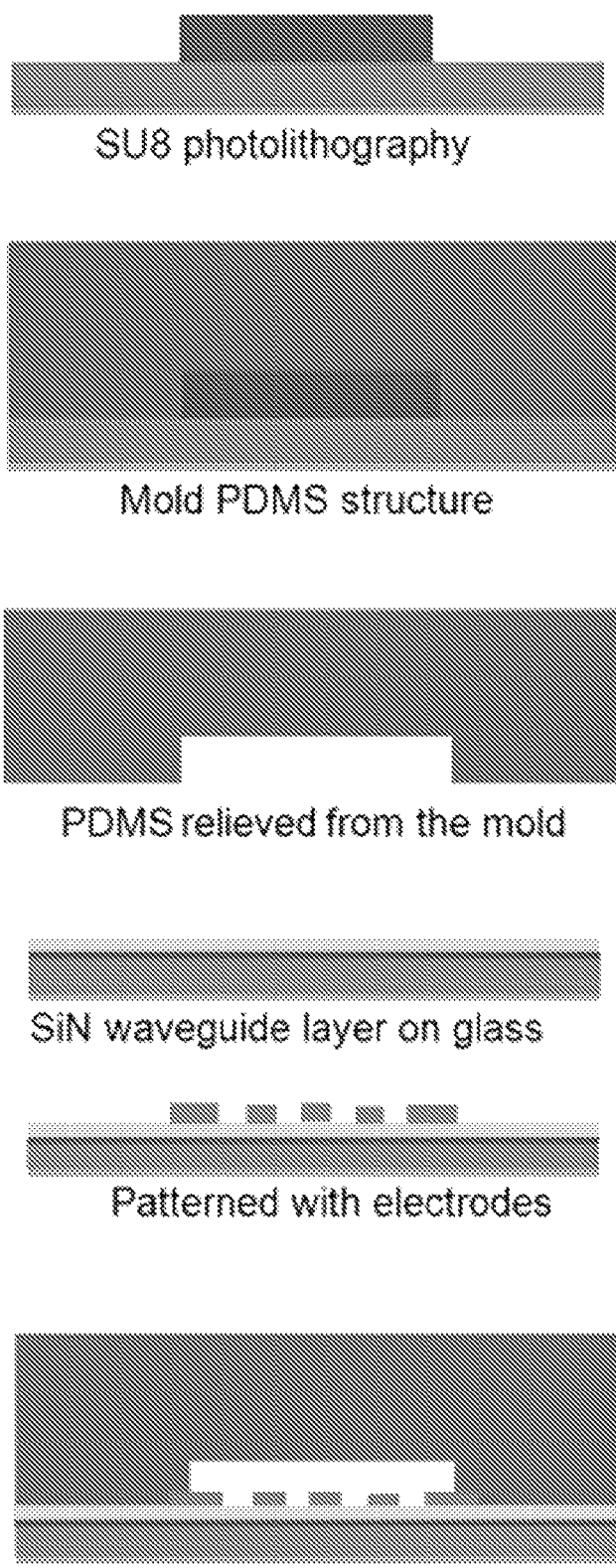
FIG. 5 shows an illustrative diagram of an exemplary fabrication process to produce the exemplary lab-on-a-chip device of FIG. 3.

FIG. 5 shows an illustrative diagram of an exemplary fabrication process to produce the exemplary lab-on-a-chip device of FIG. 3. The fabrication process includes forming a mold of the microfluidic channel and microchambers using photoresist (e.g., SU8 photoresist) via photolithographic techniques. PDMS can then be spin-coated onto the photoresist mold, e.g., after silane treatment to prevent PDMS adhesion during demolding. The PDMS structure forming the microchannel and microchambers can be removed from the photoresist mold. The fabrication process includes the patterning of glass with SiN waveguides and metal electrodes using lithography techniques. The PDMS structure is bonded to the glass substrate aligned such that the microfluidic channel is placed above the patterned electrodes that span along a substantial portion of the channel. In this example, the electrodes are formed on a glass slide bonded to the PDMS microfluidic channels. In some implementations, PDMS can be used, and in other implementations, other materials more suitable for biosensing or other clinical applications can be utilized.

In some aspects, methods, systems, and devices are described for detecting multiple circulating nucleic acids in parallel for in vitro diagnoses applications.

Circulating nucleic acids may become new biomarkers for disease diagnosis or prognosis. Expression assays of DNA and/or RNA may provide new methods for sub-classification of diseases. One major hurdle for such bioassays is the low abundance of circulating nucleic acids. For example, conventional methods that are currently used in laboratory (e.g., such as Northern blotting, reverse transcription polymerase chain reaction (RT-PCR), or microarray) are unsuitable for point-of-care applications because of the high cost and slow time of test.

Figure 6:
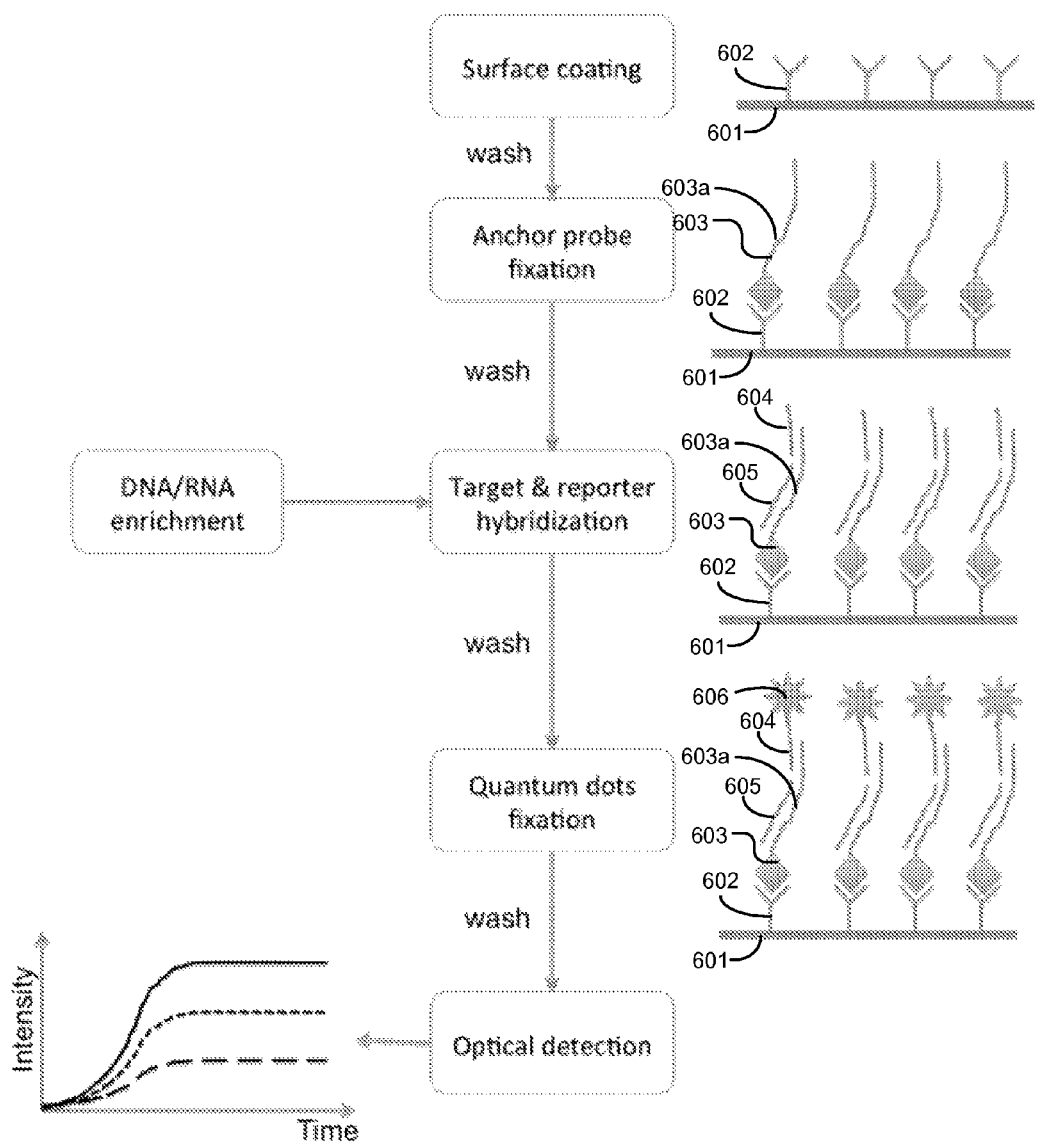
FIG. 6 shows a process flow diagram of an exemplary method for detecting circulating nucleic acids from a fluid.

FIG. 6 shows process flow diagram of an exemplary method to detect and quantify one or more circulating nucleic acid markers (e.g., DNA and/or RNA), e.g., with significant cost advantages over any existing method for similar purposes. The flow diagram of FIG. 6 also depicts an exemplary device design and its operation principle. The method includes coating the substrate or channel surface(s) 601 of an exemplary microfluidic device with a binding layer 602, e.g., such as an antibody coating (e.g., digoxigenin). The method includes introducing a fluid containing the molecular probes 603 with complimentary sequence 603a to the target DNA/RNA to the microfluidic device. The molecular probes 603 anchor to the binding layer 602 at the designated areas of the device. In some implementations, the molecular probes 603 can be configured as the molecular probe device 100 as previously described. The method includes introducing a fluid containing a reporter probe 604, e.g., which can be configured as a single stranded-DNA oligo complementary to a portion of the molecular probe sequence 603a, and the target DNA/RNA 605 from a fluidic sample brought into the microfluidic device. For example, the ss-DNA oligo reporter probe 604 will be hybridized with the end portion of the anchored probe 603. Should the target DNA/RNA 605 be present in the sample, it will also hybridize with anchored probe 603 in the section immediately next to the ss-DNA oligo reporter probe 604. Due to the short length of the reporter ss-DNA oligo probes 604 (e.g., 6-8 nts), the hybridized reporters 604 can be washed away easily. In contrast, once the target DNA/RNA 605 is hybridized with the anchored probe 603, its presence can stabilize the binding of the DNA oligo reporter probe 604 to the anchored probe 603, as a result of the "stacking effect". Those hybridized DNA oligos 604 stabilized by the stacking effect can sustain the wash process, and the biotin at the end of the reporter probe 604 can bind with the streptavidin coated quantum dots 606 introduced to the device. The method includes introducing a fluid containing a quantum dots 606 coated with streptavidin for binding to the biotinylated portion of the reporter probe 604 that indicates the binding of the target DNA/RNA 605 to the molecular probe 603. The method includes performing an optical detection of the quantum dots 606 bound to the device. For example, the method can include washing, e.g., via a buffer rinse, the microchambers or microchannels where the molecular probes 603 are anchored to the substrate 601 via the coating 602 to remove loose moieties between some or all of the steps of the described method.

Under optical excitation, for example, quantum dots 606 give rise to strong fluorescent signals that can be easily recorded by a low-cost CCD or CMOS camera mounted to a microscope. For example, each bright spot produced by a single quantum dot represents a single binding event of the target DNA/RNA 605. Therefore, the optical detection step of the exemplary method offers the sensitivity of single binding events.

In many clinical applications, for example, it is of interest to measure the population of the target DNA/RNA. In some implementations, for example, the method includes obtaining such information by using image processing software to enumerate each single bright spot from an individual quantum dot 606. In other implementations, for example, the method includes simply measuring the overall fluorescent intensity without resolving the individual bright spots. The latter approach requires no high resolution microscope and can be a cost effective solution especially attractive to clinical applications.

Figure 7:
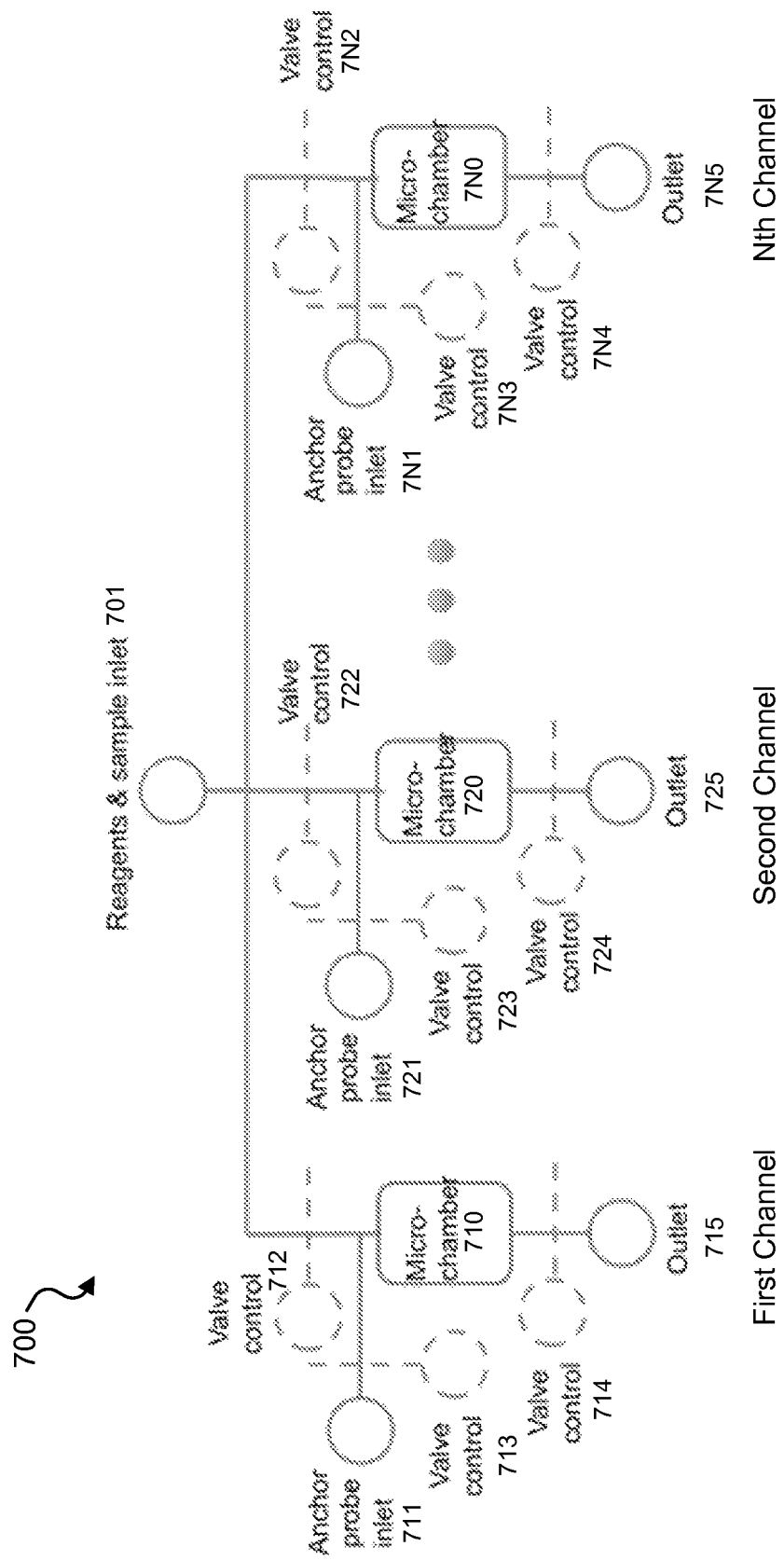
FIG. 7 shows a schematic diagram of an exemplary microfluidic device for detection of a plurality of nucleic acid targets in parallel.

FIG. 7 shows a schematic diagram of an exemplary microfluidic device 700 for detection of a plurality of nucleic acid targets in parallel. The exemplary microfluidic device 700 can provide a particularly attractive design for point-of-care circulating DNA/RNA detection based on the aforementioned detection principles. For example, the reagents and samples, except for the anchor probes, are infused from a single inlet 701. The same or a variety of specific anchor probes are infused from separate inlets 711, 721, . . . 7N1 so that each microchamber 710, 720, . . . 7N0 can detect one type of DNA/RNA target with high sensitivity and specificity. For example, with N microchambers, N nucleic acid targets can be detected. The device 700 includes three valves are used to control the fluidic flow for each micro-chamber. For example, in the first channel, the three valves include valve control 712, 713, and 714; in the second channel, the three valves include valve control 722, 723, and 724; in the Nth channel, etc. The three valves can be used to control the flow of fluids containing the reagents and samples, the flow of fluids containing the anchor probes, and the flow of fluids exiting the device 700, respectively. The dashed line in the FIG. 7 illustrates the layout of the exemplary valves located in a separate layer overlaying the microchambers to give precise sample volume control and prevent fluid evaporation during the detection process.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A molecular probe device, comprising:
a magnetic bead;
a molecular probe bound to the magnetic bead and structured to include a single-stranded nucleic acid sequence including a base pair region complimentary to a target miRNA nucleic acid that is zipped in a first position forming a hair-pinned structure in an absence of a magnetic field and that is unzipped in a second position forming an extended configuration in a presence of the magnetic field;
a binding agent to chemically bind the molecular probe to an outer surface of the magnetic bead; and
a binding molecule to chemically bind the molecular probe to a surface,
wherein the base pair region of the single-stranded nucleic acid sequence is configured to hybridize to a complementary nucleic acid sequence of the miRNA nucleic acid when the molecular probe is unzipped in the second position.

2. The device of claim 1, wherein the surface is coated with anti-digoxigenin antibody.

3. The device of claim 1, wherein the binding molecule is digoxigenin.

4. The device of claim 1, wherein the binding agent includes biotin and the magnetic bead includes a streptavidin-coated outer surface.

5. The device of claim 1, wherein the molecular probe is configured to have a short length that disfavors binding with longer RNA molecules.

6. The device of claim 1, wherein the molecular probe is structured to prohibit interaction with circulating double stranded nucleic acids.

7. The device of claim 1, wherein the molecular probe is operable to:
interact with the magnetic field via the magnetic bead such that the magnetic field attracts the magnetic bead to move and thereby unzip the base pair region to the second position to expose a base pair sequence complimentary to a base pair sequence of the target miRNA nucleic acid, and
when unzipped and exposed to the target miRNA nucleic acid, hybridize the base pair sequence of the single-stranded nucleic acid to the base pair sequence of the target miRNA nucleic acid.

8. The device of claim 7, wherein the molecular probe is configured to resist the unzipping of the hybridized base pair sequence with the target miRNA nucleic acid when the magnetic field intensity is reduced.

9. The device of claim 7, wherein the molecular probe is further operable to re-form to the hair-pinned structure in the first position when the unzipped base pair region is not hybridized to the base pair sequence of the target miRNA nucleic acid and the magnetic field intensity is reduced.

10. The device of claim 7, further comprising:
a fluorophore to emit a fluorescent signal when the molecular probe is in the second position to indicate that the target miRNA nucleic acid is hybridized to the molecular probe, wherein the fluorescent signal is quenched when the molecular probe is in the first position.

11. A device to capture, enrich, and detect biomolecules from a fluid, comprising:
a substrate formed of a material that is electrically insulating;
a microfluidic channel made of an electrically insulating material formed on the substrate to carry a biofluid containing miRNA nucleic acids;
an array of electrodes formed on the surface along a parallel direction of the microfluidic channel constituting a capture region, wherein the array of electrodes are operable to produce an electric field across the microfluidic channel that creates an electrostatic attractive force on the miRNA nucleic acids to immobilize them in the capture region;
a chamber formed on the substrate of the electrically insulating material and connected to the microfluidic channel, the chamber configured to have a volume less than that of the microfluidic channel, wherein, when the miRNA nucleic acids are released from immobilization in the capture region, the released miRNA nucleic acids are collected in the chamber at a higher concentration than that in the capture region; and
a plurality of molecular probes attached to the substrate in the chamber, the molecular probes structured to include a single stranded nucleic acid sequence having a base pair region complimentary to a target miRNA, wherein each molecular probe is coupled to a magnetic bead attached to one end of the single stranded nucleic acid sequence via a binding agent, and wherein each molecular probe is coupled to a binding molecule to chemically attach the molecular probe to the substrate in the chamber, wherein the molecular probes are zipped in a first position forming a hair-pinned structure in an absence of a magnetic field and unzipped in a second position forming an extended configuration in a presence of the magnetic field,
wherein the base pair region of the single-stranded nucleic acid sequence is configured to hybridize to a complementary nucleic acid sequence of the target miRNA in the extended position.

12. The device of claim 7, wherein the biofluid includes at least one of blood, saliva, sputum, urine, vitriol fluid, or fluid derived from a living organism.

13. The device of claim 11, wherein the microfluidic channel in the capture region is configured as a spiral-shaped channel.

14. The device of claim 11, wherein the biofluid flows through the microfluidic channel at a flow rate of 30 μL/min or less.

15. The device of claim 11, wherein the immobilized nucleic acids are released from the capture region by at least one of changing the pH of the biofluid and thereby altering the attractive force of the applied electric field or removing the applied electric field.

16. The device of claim 11, wherein the volume of the chamber is at least 1/50 of the volume of the microfluidic channel.

17. The device of claim 11, wherein the substrate in the chamber is coated with anti-digoxigenin antibody.

18. The device of claim 11, wherein the binding molecule is digoxigenin.

19. The device of claim 11, wherein the binding agent includes biotin and the magnetic bead includes a streptavidin-coated outer surface.

20. The device of claim 11, wherein the molecular probes are operable to:

interact with an applied magnetic field via the magnetic bead such that the magnetic field attracts the magnetic bead to move and thereby unzip the base pair region of the single-stranded nucleic acid sequence to expose a base pair sequence complimentary to a base pair sequence of the target miRNA, and when unzipped and exposed to the target miRNA, hybridize the base pair sequence of the single-stranded nucleic acid sequence to the base pair sequence of the target miRNA.

21. The device of claim 20, wherein the molecular probes are configured to resist the unzipping of the hybridized base pair sequence with the target miRNA when the magnetic field intensity is reduced.

22. The device of claim 20, wherein the molecular probes are further operable to re-form to the hair-pinned structure in the first position when the unzipped base pair region is not hybridized to the base pair sequence of the target miRNA and the magnetic field intensity is reduced.

* * * * *